US011135285B2

(12) United States Patent
Born van den et al.

(10) Patent No.: US 11,135,285 B2
(45) Date of Patent: Oct. 5, 2021

(54) SWINE VACCINE

(71) Applicant: Intervet Inc., Madison, NJ (US)

(72) Inventors: Erwin Born van den, Wageningen (NL); Antonius Arnoldus Christiaan Jacobs, Kessel (NL); Melanie Sno, Budapest (HU)

(73) Assignee: Intervet Inc., Madison, NJ (US)

( * ) Notice: Subject to any disclaimer, the term of this patent is extended or adjusted under 35 U.S.C. 154(b) by 151 days.

(21) Appl. No.: 16/463,990

(22) PCT Filed: Nov. 28, 2017

(86) PCT No.: PCT/EP2017/080606
§ 371 (c)(1),
(2) Date: May 24, 2019

(87) PCT Pub. No.: WO2018/099889
PCT Pub. Date: Jun. 7, 2018

(65) Prior Publication Data
US 2020/0384102 A1 Dec. 10, 2020

(30) Foreign Application Priority Data
Nov. 29, 2016 (EP) .................... 16201122

(51) Int. Cl.
*A61K 39/23* (2006.01)
*A61P 31/14* (2006.01)
*A61K 39/02* (2006.01)
*A61K 39/00* (2006.01)

(52) U.S. Cl.
CPC .......... *A61K 39/23* (2013.01); *A61K 39/0225* (2013.01); *A61K 39/0241* (2013.01); *A61P 31/14* (2018.01); *A61K 2039/54* (2013.01); *A61K 2039/545* (2013.01); *A61K 2039/552* (2013.01); *A61K 2039/70* (2013.01)

(58) Field of Classification Search
CPC ............... A61K 39/23; A61K 39/0225; A61K 39/0241; A61K 2039/54; A61K 2039/545; A61K 2039/552; A61K 2039/70; A61K 2039/55511; A61K 39/12; A61P 31/14; A61P 43/00; A61P 31/12; A61P 31/00; C12N 2750/14334; C12N 2770/10034
See application file for complete search history.

(56) References Cited

U.S. PATENT DOCUMENTS

| | | | |
|---|---|---|---|
| 5,476,778 A | 12/1995 | Chladek et al. | |
| 6,042,830 A * | 3/2000 | Chladek | C07K 16/10 424/184.1 |
| 2002/0025325 A1 * | 2/2002 | Chu | A61K 9/0095 424/204.1 |
| 2004/0009190 A1 * | 1/2004 | Elbers | C07K 14/005 424/199.1 |
| 2005/0079185 A1 * | 4/2005 | Parisot | A61P 31/00 424/184.1 |
| 2006/0171960 A1 * | 8/2006 | Chu | A61P 37/04 424/202.1 |
| 2006/0204522 A1 * | 9/2006 | Kroll | C12N 7/00 424/201.1 |
| 2006/0233831 A1 * | 10/2006 | Parisot | A61P 31/04 424/204.1 |
| 2008/0226669 A1 * | 9/2008 | Roof | A61P 37/04 424/201.1 |
| 2010/0062019 A1 * | 3/2010 | Parisot | A61K 39/12 424/209.1 |
| 2017/0014513 A1 * | 1/2017 | O'Connell | A61K 39/225 |

FOREIGN PATENT DOCUMENTS

RU 2166327 C2 5/2001

OTHER PUBLICATIONS

Jacobs A, Harks F, Hoeijmakers M, Segers R. A novel octavalent combined Erysipelas, Parvo and Leptospira vaccine provides (cross) protection against infection following challenge of pigs with 9 different Leptospira interrogans serovars. Porcine Health Manag. Nov. 17, 2015;1:16. (Year: 2015).*
Charerntantanakul W. Porcine reproductive and respiratory syndrome virus vaccines: Immunogenicity, efficacy and safety aspects. World J Virol. Feb. 12, 2012;1(1):23-30.*
Young B, Dewey C, Poljak Z, Rosendal T, Carman S. Clinical signs and their association with herd demographics and porcine reproductive and respiratory syndrome (PRRS) control strategies in PRRS PCR-positive swine herds in Ontario. Can J Vet Res. Jul. 2010;74(3):170-7.*
Lambert ME. Épidémiologie du syndrome reproducteur et respiratoire porcin dans deux régions de densités porcines différentes au Québec. PhD Dissertation, University of Montreal. Jun. 2011.*
Boehringer Ingelheim—Porcine Reproductive andRespiratory SyndromeParvovirus Vaccine Reproductive Form, Modified Live and Killed Virus Erysipelothrix Rhusiopathiaeleptospira Canicola Grippotyphosa-Hardjolcterohaemorrhagiae PomonaBacterin—Jan. 20, 2012—pp. 1-2.
Charerntantanakul, W, Porcine reproductive and respiratory syndrome virus vaccines: Immunogenicity, efficacy and safety aspercts, World journal of Virology, Jan. 1, 2012, pp. 23, vol. 1, No. 1.
International Search Report for application PCT/EP2017/080606 dated Jan. 17, 2018, 4 pages.

(Continued)

*Primary Examiner* — Rachel B Gill
(74) *Attorney, Agent, or Firm* — Michael D. Davis

(57) ABSTRACT

The invention pertains to a vaccine comprising in combination non-replicating immunogens of *Erysipelothrix rhusiopathiae*, porcine parvo virus, *Leptospira interrogans* and live attenuated PRRS virus, and a pharmaceutically acceptable carrier, for use in a method for prophylactic treatment of a swine against an infection with *Erysipelothrix rhusiopathiae*, porcine parvo virus, *Leptospira interrogans* and PRRS virus, wherein the vaccine is administered in a single dose with regard to the treatment against an infection with PRRS virus.

9 Claims, No Drawings

(56) References Cited

OTHER PUBLICATIONS

Jacobs, A et al, Safety and efficacy of a new octavalent combined Erysipelas, Parvo and Leptospira vaccine in gilts against Leptospira interrogans serovar Pomona associated disease and foetal death, Vaccine, 2015, pp. 3963-3969, vol. 33, Elsevier.

Pfizer—Material Safety Data Sheet for Product Farrowsure B—May 10, 2004—pp. 1-7—Internet Citation—www.pfizerah.com.

Puig et al—Vaccination with the mixed administration of eryseng parvo unistrain PRRS in gilts clinically protects against a heterologus PRRSV infection—Jun. 11, 2015—Retrieved from the internet—http://info.hipra.com/DOCS/UNISTRAIN/Publications/ESPHM-2015/1-Clinical-protection.pdf.

Vetvac—a Free Online Database of Livestock Veterinary Vaccines—Entry for Reprocyc Rpps Ple—Jan. 1, 2010—Retrieved From the Internet www.vetvac.org.

\* cited by examiner

SWINE VACCINE

CROSS-REFERENCE TO RELATED APPLICATIONS

This application is a national stage entry under 35 U.S.C. § 371 of PCT/EP2017/080606, filed on Nov. 28, 2017, which claims priority to EP Application 16201122.5, filed on Nov. 29, 2016, the content of PCT/EP2017/080606 is hereby incorporated by reference in its entirety.

GENERAL FIELD OF THE INVENTION

The invention in general pertains to the field of swine health. Swine are prone to many pathogenic micro-organisms. Control of infection is commonly done by stable and feed management, treatment with pharmaceuticals such as anti-viral drugs and antibiotics, or prophylactic treatment using vaccines. In particular, the invention pertains to vaccines against PRRS (porcine reproductive and respiratory syndrome) virus, *Erysipelothrix rhusiopathiae*, porcine parvo virus and *Leptospira interrogans* (Sensu Lato), and to a method of protecting an animal against such infections using such vaccines.

BACKGROUND OF THE INVENTION

PRRS virus was first reported in 1987 in North America and Central Europe. PRRS virus is a small, enveloped RNA virus. It contains a single-stranded, positive-sense, RNA genome with a size of approximately 15 kilobases. The genome contains nine open reading frames. The virus is a member of the genus Arterivirus, family Arteriviridae, order Nidovirales. The two prototype strains of PRRSV are the North American strain, VR-2332, and the European strain, the Lelystad virus (LV). The European and North American PRRSV strains cause similar clinical symptoms. In the early 2000s a highly pathogenic strain of the North American genotype emerged in China. This strain, HP-PRRSV, is more virulent than all other strains, and causes great losses in Asian countries worldwide. Clinical signs include reproductive failure in sows such as abortions and giving birth to stillborn or mummified foetuses, and cyanosis of the ear and vulva. In neonatal pigs, the disease causes respiratory distress, with increased susceptibility to respiratory infections such as Glasser's disease. Regarding PRRS virus, although inactivated virus vaccines have been described and are commercially available, Modified Live Virus (MLV) comprising either the European type (type I) or the North American type (type II) in live attenuated form, are the primary immunological tool for its control. Several vaccines are commercially available in the art. Porcilis® PRRS (available from MSD Animal Health, Boxmeer, The Netherlands) is a vaccine comprising live attenuated PRRS virus type I and is registered to reduce infection (viraemia) caused by infection with PRRS virus. Ingelvac PRRS® MLV (available from Boehringer Ingelheim, Ingelheim, Germany) is a vaccine that aids in the reduction of disease caused by PRRS virus. Fostera® PRRS (available from Zoetis, Florham Park, N.J., USA) is also a MLV vaccine and is registered for protection against both the respiratory and reproductive forms of disease caused by PRRS virus. Other PRRS vaccines are described for example in WO2006/074986, U.S. Pat. No. 8,728,487 and WO2014/048955.

Infectious disease caused by *Erysipelothrix rhusiopathiae* (Ery) in pigs is known as erysipelas and is one of the oldest recognized diseases that affect growing and adult swine. Up to 50% of pigs in intensive swine production areas are considered to be colonized with Ery. The organism commonly resides in the tonsillar tissue. These typical healthy carriers can shed the organism in their faeces or oronasal secretions and are an important source of infection for other pigs. Disease outbreaks may be acute or chronic, and clinically inapparent infections also occur. Acute outbreaks are characterized by sudden and unexpected deaths, febrile episodes, painful joints, and skin lesions that vary from generalized cyanosis to the often-described diamond skin (rhomboid urticaria) lesions. Chronic erysipelas tends to follow acute outbreaks and is characterized by enlarged joints and lameness. A second form of chronic erysipelas is vegetative valvular endocarditis. Pigs with valvular lesions may exhibit few clinical signs; however, when exerted physically they may show signs of respiratory distress, lethargy, and cyanosis, and possibly suddenly succumb to the infection. Acutely affected pregnant sows may abort, probably due to the fever. Vaccination is very effective in controlling disease outbreaks. Injectable bacterins and other non-replicating immunogens are known and provide a long duration of immunity. Commercial available vaccines comprising non-replicating immunogens of *Erysipelothrix rhusiopathiae* are Porcilis® ERY+Parvo (MSD Animal Health), FarrowSure® Gold (Zoetis), ErySeng® Parvo (Hipra) and PARVORUVAX® (Merial). Optimal timing of vaccination may vary from farm to farm. Susceptible pigs may be vaccinated before weaning, at weaning, or several weeks after weaning. Male and female swine selected for addition to the breeding herd should preferably be vaccinated with a booster 3 to 5 weeks later. Thereafter, breeding stock should be vaccinated twice yearly. In general there is good cross-protection among the major *Erysipelothrix rhusiopathiae* strains infecting pigs.

Porcine parvovirus is ubiquitous in pigs around the world. Almost all females are naturally infected before their second pregnancy, and immunity is lifelong. Consequently, it is a disease typical for first-parity pigs. Gilts that are immunologically naive or have high passive antibody titers have the highest risk of reproductive disorders caused by the virus. Infection before day 30 of pregnancy results in early embryonic loss. Fetal infection between 30 and 70 days of gestation can result in death of the fetus and mummification. Not all fetuses are infected at the same time, and death at different stages of pregnancy is typical. Some fetuses survive and are born alive but persistently infected. Most fetuses infected after 70 days of gestation mount an immune response, clear the virus, and are healthy at birth. Litters with dead fetuses of varying sizes, including mummified fetuses, along with stillborn and healthy pigs born to first-parity gilts, are the hallmark of porcine parvovirus. Diagnosis is by fluorescent antibody testing, virus isolation using lung from mummified fetuses, or demonstration of precolostral antibody in stillborn pigs. Boars shed virus by varying routes, including semen, for a couple of weeks after acute infection and can introduce the virus into a herd. Effective vaccines comprising non-replicating immunogens are widely available, such as for example Porcilis® ERY+Parvo (MSD Animal Health), FarrowSure® Gold (Zoetis), and PARVORUVAX® (Merial).

*Leptospira interrogans* (Sensu Lato, i.e. all pathogenic *leptospira* bacteria), especially serogroup Pomona, is a major cause of reproductive failure in swine (infertility, abortion, stillbirths, and the birth of weak piglets). Although acute leptospirosis occurs in adult swine, most cases are asymptomatic. Pigs infected with serogroups Pomona and *Australis*, serovar Bratislava, can become chronic renal carriers. Abortion occurs 1 to 4 weeks after infection, and the faetuses are autolyzed. Mummification, maceration, stillbirths, and weak pigs are also seen. Diagnosis is based on demonstration of leptospires in fetal tissues or stomach contents. However, severely autolyzed fetuses may result in poor fluorescent antibody and immunohistochemistry results. PCR testing has better sensitivity and specificity. Vaccination with a (multivalent) bacterin or other non-replicating immunogen, typically every 6 to 12 months, helps mitigate or even prevent leptospirosis. Field results indicate that *Leptospira* infection cannot be reliably eliminated with antibiotics. Effective vaccines can be obtained commercially, e.g. FarrowSure® Gold and Lepto-Eryvac® (Zoetis), and Porcilis® Ery+Parvo+Lepto (MSD Animal Health).

OBJECT OF THE INVENTION

There is a continuous need for convenient, safe and efficacious means for the management of swine health. In particular, there is a need for a convenient, safe and efficacious vaccine that can be used for prophylactic treatment of a swine against an infection with *Erysipelothrix rhusiopathiae*, porcine parvo virus, *Leptospira interrogans* and PRRS virus. Infections with these pathogens in particular may decrease the reproductive performance of female swine.

SUMMARY OF THE INVENTION

In order to meet the object of the invention a new vaccine for the protection of swine against infections with various disease causing micro-organisms is devised, the vaccine comprising in combination non-replicating immunogens of *Erysipelothrix rhusiopathiae*, porcine parvo virus, *Leptospira interrogans* and live attenuated PRRS virus, and a pharmaceutically acceptable carrier wherein the vaccine is administered in a single dose with regard to the treatment against an infection with PRRS virus. This vaccine is very suitable to be used in female swine for improving their reproductive performance.

According to the invention, the vaccine is administered in a single dose with regard to the treatment against an infection with PRRS virus. It was advantageously found that a swine can be vaccinated successfully with the combination vaccine against PRRS virus infection even after a single shot administration of the vaccine. This does not exclude that a follow up vaccination is given, for example 6 to 12 months after the first vaccination to renew the level of protection. This follow up vaccination differs from a boost vaccination in a prime-boost vaccination scheme, wherein protection is only believed to be obtained after the boost vaccination. In a prime-boost scheme, the two vaccinations are typically 2-4 weeks apart.

Although vaccines are known and commercially available to treat *Erysipelothrix rhusiopathiae*, porcine parvo virus, *Leptospira interrogans* and PRRS virus infections, there is a continuous need for novel ways to provide good protection in a safe and convenient way. A combination vaccine against all of these pathogens is commercially available in the US (ReproCyc® PRRS-PLE of Boehringer Ingelheim). However, this is a two shot vaccine for all of the antigens in order to arrive at adequate protection (vaccination needs to be repeated within 3-4 weeks). Next to this, even the two-shot administration regime as described in the art is only successful when the animals are PRRS virus positive, thus when it is clear that their immune system is already (pre-) primed with the virus. The known administration scheme is thus in fact a three-shot immunisation scheme. Indeed, PRRS virus is an immune evasive virus against which adequate protection is not easy to arrive at. Surprisingly applicant found that a one shot vaccination is sufficient when using a live attenuated PRRS virus in combination with the Ery, paro and Lepto antigens, even in PRRS virus negative animals. This is not understood, but may be a result of positive antigen interference. Moreover, It is always uncertain whether a combination of antigens contemplated or suggested may lead to a safe and effective combination vaccine in any novel administration regime, mainly due to unpredictable interference effects of the antigens. In fact, there is always a level of uncertainty with regard to safety and efficacy of any contemplated combination vaccine in any particular administration regime.

The committee for veterinary medicinal products of the European Agency for the Evaluation of Medicinal Products (EMEA) in its publication "Note for guidance: requirements for combined veterinary products" (EMEA, 2000, CVMP/IWP/52/97-FINAL), stated (page 2/6) that the "development of combined vaccines is not straightforward. Each combination should be developed and studied individually in terms of quality, safety and efficacy". The committee further indicates that the search for a good combination vaccine typically includes the compatibility between the individual components in the combined vaccine, including for example preservatives, excipients and stabilisers, inactivating agents and adjuvants. On page 3, top paragraph, it is stated that "In combined vaccines, the presence of more than one component can often cause an interaction, leading to either a diminished or an increased response to individual components, compared to when the specific component(s) is administered alone . . . . Such interactions are often immunological in nature, but may also be caused by other factors with less direct effects on the immune system".

The U.S. Department of Health and Human Services, Food and Drug Administration, Center for Biologics Evaluation and Research, published in April 1997 a "Guidance for Industry, for the evaluation of combination vaccines for preventable diseases: Production, Testing and Clinical Studies", in which guidance it is stated (page 3, under "Compatibility of Components") that "Experience has shown that combining monovalent vaccines may result in a new combination which is less safe or effective than desirable. Sometimes the components of inactivated vaccines may act adversely on one or more of the active components", indicating that especially an inactivated vaccine may negatively influence the efficacy of a live vaccine, such as for example occurred when combining a live pertussis vaccine and an inactivated poliovirus vaccine that resulted in a vaccine with decreased pertussis potency. It is indicated that any additional components in the vaccine might complicate the safety and potency of the final product when compared to the individual vaccines.

The World Health Organization (WHO) has published an e-learning course called "Vaccine Safety Basics", which in the MODULE 2 contemplates combination vaccines. This module starts with "Licensed combination vaccines undergo extensive testing before approval by national authorities to assure that the products are safe, effective, and of acceptable quality." It is also stated that "With all combinations, manufacturers must therefore evaluate the potency of each antigenic component, the effectiveness of the vaccine components when combined to induce immunity, risk of possible reversion to toxicity, and reaction with other vaccine components."

All in all, any combination of particular antigens is not straightforward and requires experimentation to determine safety and efficacy.

The present invention, next to the vaccine as such, also pertains to a combination vaccine for use in a method for prophylactic treatment of a swine against an infection with *Erysipelothrix rhusiopathiae*, porcine parvo virus, *Leptospira interrogans* and PRRS virus, to a method to constitute such a vaccine and to a method for prophylactic treatment of a swine against an infection with *Erysipelothrix rhusiopathiae*, porcine parvo virus, *Leptospira interrogans* and PRRS virus, comprising administering the said vaccine to the animal, in particular a single dose with regard to PRRS virus, parenterally, in particular intramuscularly.

The invention also pertains to a combination of a first vaccine comprising non-replicating immunogens of *Erysipelothrix rhusiopathiae*, porcine parvo virus and *Leptospira interrogans*, and a pharmaceutically acceptable carrier, and a second vaccine comprising freeze-dried live attenuated PRRS virus, and an instruction that the second vaccine can be mixed with the first vaccine to form the vaccine according to the invention. In practice the first and second vaccine may be sold as separate, stand-alone vaccines, but having an indication on the label, package leaflet or otherwise, that the two vaccines can be mixed to form one multi-way combination vaccine, wherein the vaccine is administered in a single dose with regard to the treatment against an infection with PRRS virus.

Definitions

A vaccine is a pharmaceutical composition that is safe to administer to a subject animal, and is able to induce protective immunity in that animal against a pathogenic microorganism (a "pathogen"), i.e. to induce a successful prophylactic treatment against an infection with the pathogen as defined here below. A vaccine may be used in conjunction with an adjuvant, i.e. a substance or composition that is able to increase the immune response induced by the vaccine.

Non-replicating immunogen of a pathogen is any substance or compound corresponding to the pathogen, other than the live replicating pathogen as a whole (either in wild type or attenuated form), against which pathogen an immunological response is to be elicited, such that the corresponding virulent pathogen or one or more of its virulence factors will be recognized by the host's immune system as a result of this immune response and are ultimately, at least partly, neutralized. Typical examples of non-replicating immunogens are inactivated (killed) whole pathogens and subunits of these pathogens such as capsid proteins and surface expressed proteins, for example recombinantly expressed proteins. Non-replicating immunogens (e.g. killed whole pathogen, cell lysate, subunit, etc.) evoke an immune response that is primarily of the humoral type (i.e. induction of antibodies).

Prophylactic treatment against an infection with a pathogen is aiding in preventing or ameliorating an infection with that pathogen or a disorder arising from that infection, resulting from a post treatment challenge with a pathogen, in particular to reduce its load in the host after such challenge and optionally to aid in preventing or ameliorating one or more clinical manifestations resulting from the post treatment infection with the pathogen.

A live attenuated pathogen is a viable, replication competent form of the pathogen having reduced virulence. The process of attenuation takes an infectious pathogen and alters it so that it becomes harmless or less virulent, typically by either multiple passages of the pathogen through cell systems or by genetically modifying the pathogen.

Single dose administration of a vaccine for use in prophylactic treatment means that in order to arrive at protective immunity, the vaccination does not need to be boosted with a second administration of the vaccine. In a two-shot regime, the first (prime) vaccination is typically boosted within 6 weeks from the first administration, commonly within 3 or even 2 weeks from the first administration, and only after the second (boost) administration protective immunity, i.e. a successful prophylactic treatment as defined here above, may be obtained.

A pharmaceutically acceptable carrier is a biocompatible medium, viz. a medium that after administration does not induce significant adverse reactions in the subject animal, capable of presenting the antigen to the immune system of the host animal after administration of the vaccine. Such a carrier can be a liquid containing water and/or any other biocompatible solvent, possibly forming an emulsion with one or more hydrophobic liquids such as an oil. The carrier however can also be a solid such as commonly used to obtain freeze-dried vaccines (based on sugars and/or proteins).

EMBODIMENTS OF THE INVENTION

In an embodiment, the non-replicating immunogens of *Erysipelothrix rhusiopathiae*, porcine parvo virus, *Leptospira interrogans* are inactivated pathogens of *Erysipelothrix rhusiopathiae*, porcine parvo virus and *Leptospira interrogans* respectively. For example by simply killing the pathogens, a simple way is provided to have (all) immunogens available in a non-replicating form. Although any subunit vaccine might also be suitable for use in the present vaccine, by having the inactivated pathogens available, the relevant immunogens are present per se, and in a way (similar to the way wherein) they are present in the live, naturally occurring pathogen.

In a further embodiment, the *Leptospira interrogans* pathogen comprises bacteria of the serogroup Pomona, which is the most important swine *leptospira* pathogen. Optionally bacteria of at least one the serogroups Tarassovi, *Australis*, Grippotyphosa, Icterohaemorrhagiae and *Canicola*, are also present, wherein the bacteria of the serogroup *Australis* in particular are bacteria of the serovar Bratislava.

As indicated here above, also in a further embodiment the vaccine for use in a method for prophylactic treatment of a swine against an infection with *Erysipelothrix rhusiopathiae*, porcine parvo virus, *Leptospira interrogans* and PRRS virus, the non-replicating immunogens of *Erysipelothrix rhusiopathiae*, porcine parvo virus, *Leptospira interrogans* are inactivated (e.g. killed) pathogens. In particular, the *Leptospira interrogans* pathogen comprises bacteria of the serogroup Pomona, and optionally bacteria of at least one the serogroups Tarassovi, *Australis*, Grippotyphosa, Icterohaemorrhagiae and *Canicola*, wherein the bacteria of the serogroup *Australis* in particular are bacteria of the serovar Bratislava.

In still another embodiment the vaccine is administered parenterally, i.e. administered elsewhere to the body than the mouth and alimentary canal. The vaccine can for example be administered intramuscularly.

As stated here above, the invention also pertains to a method to constitute the combination vaccine wherein the method comprises mixing a first composition comprising live attenuated PRRS virus with a second composition comprising the immunogens of *Erysipelothrix rhu-*

*siopathiae*, porcine parvo virus, and *Leptospira interrogans* in the pharmaceutically acceptable carrier. In a further embodiment the first composition comprises freeze-dried PRRS virus, for example in a stabiliser such as known from Porcilis® PRRS. The mixing takes preferably place at most 24 hours before the vaccine is administered to the animal, or at most 12, 11, 10, 9, 8, 7, 6, 5, 4, 3, 2, 1, or ½ an hour before administration is due to take place.

The invention will now be explained in more detailed, using the following examples.

EXAMPLES

Experiment 1: The Combination of Non-Live Immunogens of Ery, Parvo and Lepto In a first experiment, the safety and efficacy of the combination of non-replicating immunogens of *Erysipelothrix rhusiopathiae*, porcine parvo virus, *Leptospira interrogans* was assessed. For such a combination of non-live antigens, in particular safety is an important aspect. This is because of the relatively high amount of antigens that is typically used in such a (non-live) vaccine, with the risk of an endotoxic shock, in particular when the immunogens comprise inactivated pathogens of gram-negative bacteria (which bacteria the cells walls comprise endotoxic lipopolysaccharides).

The study was designed as a historically controlled field study. It was conducted on a farm with a history of increased abortion rates, associated with *leptospira* infection. High antibody titres against serogroup Pomona were found in a number of animals indicating a recent *Leptospira* serogroup Pomona infection. The farm was negative for PRRS virus infection.

At the start of the study, all breeding sows and replacement gilts on the farm were vaccinated in the neck muscle twice, with an interval of 4 weeks, with a vaccine containing non-replicating immunogens of *Erysipelothrix rhusiopathiae* (formalin inactivated bacteria, strain M2), porcine parvo virus (BPL inactivated virus, strain 014) and *Leptospira interrogans* (BPL inactivated bacteria of the serogroups Pomona, Tarassovi, *Australis* (serovar Bratislava), Grippotyphosa, lcterohaemorrhagiae and *Canicola*) in an aqueous dl-α-tocopherol-acetate based adjuvant. This vaccine composition is denoted as "Ery/parvo/lepto". The animals were re-vaccinated with Ery/parvo/lepto in the second week of every following lactation. New replacement gilts were vaccinated using the same schedule.

The reproductive performance of the pigs in the study was monitored. The farrowing results and relevant breeding data were collected to determine if vaccination had any effect on the incidence of abortion. The results obtained during the study period were compared to the historical data. Since parvovirus and Ery also have a significant negative impact on reproduction (parvo may kill the foetuses and Ery may cause abortion), a substantial improvement in this respect is a good indication that the vaccine is also effective against these pathogens.

No adverse events were reported during the study, indicating that the vaccine was safe. Regarding efficacy, the percentage abortions between the study period and the pre-study period were compared, taking into consideration the effect of season. After vaccination a rapid improvement on abortions was manifested, from 12.6% pre-vaccination, down to 0.5% after vaccination had started. This is a decrease in abortion rate of 96%. The total number of abortions on the farm decreased from 55 to 6. The trend of having a low number of abortions at the farm was stable after the vaccination program started and in the following season. The frequency of abortions remained low, viz. 0.6%. The safety and efficacy of the vaccine was confirmed in another study reported in Porcine Health management in November 2015 (Porcine Health Management 2015 1:16/ DOI: 10.1186/s40813-015-0011-0). This study focused on viraemia, renal infection and urinary shedding.

It may thus be concluded that the vaccine comprising in combination non-replicating immunogens of *Erysipelothrix rhusiopathiae*, porcine parvo virus and *Leptospira interrogans* is safe and efficacious against all of these pathogens. Adding a live PRRS virus to this vaccine, which (inherently) contains a relatively low amount of antigen when compared to the inactivated pathogens of ery/parvo/lepto, it is not expected that there is a negative effect on the efficacy of the ery/parvo/lepto immunogens. However, safety might be compromised and the effect of the inactivated immunogens on the live PRRS virus is not known and needs to be assessed. This was done in another experiment, of which the results are indicated here below.

Experiment 2: The Effect of the EPL Combination Vaccine on Live PRRS Vaccine The objective of this study was to evaluate the vaccine potential in six-week-old SPF piglets of a live attenuated Porcine Reproductive and Respiratory Syndrome Virus (PRRSV) Type 1 vaccine (Porcilis PRRS) reconstitution in a vaccine comprising in combination non replicating immunogens of *Erysipelothrix rhusiopathiae*, porcine parvo virus and *Leptospira interrogans*.

The study was performed with forty PRRSV antibody negative piglets, evenly distributed over 2 groups. Groups 1 and 2 were vaccinated once intramuscularly (IM) with 2 ml Porcilis PRRS diluted to 4.5 $\log_{10}$ $TCID_{50}$ per dose (this dose represents a dose slightly above minimal dose of 4.0 $\log_{10}$ $TCID_{50}$ for Porcilis® PRRS). Group 1 received the PRRS vaccine diluted in an experimental Ery/Parvo/Lepto combination vaccine as indicated here above in experiment 1. The vaccines were mixed at a temperature of 25° C. and left for at least 1 hour before actual administration to the animals. Group 2 received the live attenuated virus diluted in Diluvac Forte, and thus de facto received the regular vaccine Porcilis® PRRS slightly above its minimal dose. This group in fact served as a positive control.

The following parameters were measured: local and systemic reactions, PRRSV viremia and PRRSV serology. This way, it can be established whether the vaccine strain is able to normally replicate in the host animal, which is a requisite for induction of an effective immune response. From the day of vaccination onwards until the end of the experiment (28 days post vaccination, dpv), all piglets were observed daily for clinical signs. Blood samples were collected just before vaccination, and 2 and 4 weeks post vaccination. Serum samples obtained at time points after vaccination were used to determine PRRSV-specific viremia and serological responses.

Veterinary examination showed that all piglets were healthy on the day of vaccination. No adverse events which could be related to the vaccination were found. One piglet in group 2 was found dead on the evening post blood sampling at 14 days post vaccination. Necropsy was performed and cause of death was most likely a hematoma in the neck, due to blood sampling.

The PRRS virus serology results are indicated in Table 1. The PRRS virus viraemia results are indicated in Table 2.

TABLE 1

PRRSV serology results: percentage of positive animals, 0, 14 and 28 dpv

| Group | 0 dpv | 14 dpv | 28 dpv |
|---|---|---|---|
| 1 | 0 | 80 | 100 |
| 2 (positive control) | 10 | 100 | 100 |

TABLE 2

PRRSV viraemia results: percentage of positive animals, 14 and 28 dpv

| Group | 14 dpv | 28 dpv |
|---|---|---|
| 1 | 70 | 100 |
| 2 (positive control) | 100 | 100 |

It appeared that the serology as well as the viraemia results for PPRS virus of the combination vaccine was comparable to that of the positive control (Porcilis® PRRS as a stand alone vaccination), both at the minimum protective dose as well as the higher dose. These data thus indicate that the PRRS virus is able to survive incubation in a vaccine comprising in combination non replicating immunogens of *Erysipelothrix rhusiopathiae*, porcine parvo virus and *Leptospira interrogans*. Based on these data, it is understood that a (two-way) combination vaccine comprising non-replicating immunogens of *Erysipelothrix rhusiopathiae* and live attenuated PRRS virus will also be safe and effective. To this vaccine, non-replicating immunogens of porcine parvo virus may be added to provide also protection against an infection with porcine parvo virus. Such a three-way vaccine is also understood to be safe and effective based on the present results. This all provides a number of different vaccines which enable to help in providing the following vaccination schemes for swine, specifically directed at enhancing reproductive performance of these animals: a basic vaccination, for example a prime-boost vaccination, of an animal before its first gestation (typically between 20 and 30 weeks of age) with a combination vaccine comprising non-replicating immunogens of *Erysipelothrix rhusiopathiae*, porcine parvo virus and *Leptospira interrogans*, wherein, if a prime-boost scheme is used, either the prime or boost vaccine is combined with live attenuated PRRS virus in line with the present invention (the PRRS component of the vaccine in any case being used as a single dose vaccine). A prime-boost vaccination could for example take place at 20 and 24 weeks age. This basic vaccination could then be repeated yearly against ery/parvo/lepto/prrs infection with a single dose of the combination vaccine according to the present invention, or with a combination vaccine wherein, depending on the circumstances, one or more of the antigens are not present (for example no *leptospira* antigens if a farm is not expected to be infected with any *leptospira* bacteria). Regarding PRRS, depending on the PRRS infection pressure on the farm, vaccination could be repeated every 6 months (or even every 3 months) if deemed necessary. Such a re-vaccination at a shorter interval could be done with a combination vaccine comprising next to the live attenuated PRRS virus, non-replicating immunogens of *Erysipelothrix rhusiopathiae*. For *leptospira* and parvo virus such a short term re-vaccination is typically not regarded as necessary since *leptospira* and parvo vaccines may have a duration of immunity of about a year in swine.

In conclusion, it can be said that the safety as well as the efficacy of the novel combination vaccine is sufficient. Additional serology data (in particular for porcine parvo virus and *leptospira* bacteria) and/or challenge data (in particular for PRRS virus and *Erysipelothrix rhusiopathiae*) may be used to confirm the efficacy of the new combination vaccine for each of the corresponding pathogens.

Experiment 3: Serology Results of the EPL/PRRS Combination Vaccine

The objective of this experiment was to confirm the serological response of associated mixed use of a Ery+Parvo+Lepto vaccine (Porcilis® Ery+Parvo+Lepto) with a live PRRS vaccine (Porcilis® PRRS) compared to the separate vaccines. Porcilis® PRRS normally is administered once whereas the basic vaccination of Porcilis® Ery+Parvo+Lepto (EPL) consists of two vaccinations with a 4-week interval. Thus Porcilis® PRRS can be co-administered during EPL primary vaccination or during the EPL booster vaccination. Both mixing options have been tested in this study.

For this study sixty-four 20 week-old pigs (sero-negative for all vaccine components) were used and allotted to 4 groups of 16 animals each. Group 1 was vaccinated with Porcilis EPL+Porcilis PRRS at 20 w of age and with Porcilis EPL at 24 w of age. Group 2 was vaccinated with Porcilis EPL at 20 w of age and with Porcilis EPL+Porcilis PRRS at 24 w of age. Group 3 was vaccinated with Porcilis EPL at 20 w of age and at 24 w of age. Group 4 was vaccinated with Porcilis PRRS at 20 w of age. During one 20 w after vaccination blood was sampled regularly and the sera were tested in the respective serological tests.

The test was valid if the animals are seronegative at the start of the study and if at least 10 animals in each control group remains sero-negative for the component omitted from the vaccinations i.e. group 4 negative for Ery, parvo and *Leptospira* and group 3 negative for PRRS. These criteria were fulfilled. The overall results per antigen are described here below.

PRRS Serology (Using the PRRS X3 Test, IDEXX)

At the start of the study most animals were seronegative. The responses after the associated mixed use vaccinations (group 1 and 2) were at least as good as for Porcilis PRRS alone (group 4), whereas the Porcilis Ery+parvo+Lepto alone group 3 remained at a low level. Therefore, it can be concluded that the associated mixed use at 20 w or at 24 w of age had no negative effect on the PRRS component of Porcilis PRRS.

Ery Serology (Using the CIVTEST Suis SE/MR, Hipra)

At the start of the study most animals were seronegative. The responses after the associated mixed use vaccinations (group 1 and 2) were at least as good as for Porcilis Ery+Parvo+Lepto alone (group 3), whereas the Porcilis PRRS alone group 4 remained at a low level. Therefore, it can be concluded that the associated mixed use at 20 w or at 24 w of age had no negative effect on the Ery component of Porcilis Ery+Parvo+Lepto.

Parvo Serology (Using an in House HI Test and the INgezim PPV Test, Ingenasa)

Although the HI test is often used to detect post-infection Parvo antibodies it is less suitable for post-vaccination serological studies because after vaccination many nonresponders are found. Therefore, this antigen was tested in the HI test as well as in a more sensitive commercially available ELISA.

At the start of the study most animals were seronegative in both tests. The responses after the associated mixed use vaccinations (group 1 and 2) were at least as good as for Porcilis Ery+Parvo+Lepto alone (group 3), whereas the Porcilis PRRS alone group 4 remained at a low level. Therefore it can be concluded that the associated mixed use at 20 w or at 24 w of age had no negative effect on the Parvo component of Porcilis Ery+Parvo+Lepto.

Lepto Serology (Using in House Serogroup Specific ELISA's)

The MAT (micro agglutination) test is generally used to detect post-infection *Leptospira* antibodies. However, this test mainly measures IgM antibodies which are shortly lived and predominantly induced after primary vaccination, whereas mainly IgG antibodies are induced after a booster vaccination. In addition, some serotypes do hardly respond in the MAT test which also makes this test less suitable for serological studies. Because IgG has been implicated in protection and because the MAT test is less suitable, serotype specific antibody ELISA's were in-house developed and validated. These serotype specific inhibition ELISA's were used to measure serotype specific IgG responses in this study.

At the start of the study all animals were seronegative. The responses after the associated mixed use vaccinations (group 1 and 2) were at least as good as Porcilis Ery+Parvo+Lepto alone (group 3), whereas the Porcilis PRRS alone group 4 remained at a low level. Therefore, it can be concluded that the associated mixed use at 20 w or at 24 w of age had no negative effect on any of the Lepto components of Porcilis Ery+Parvo+Lepto. In addition, the decline in antibody titre over time gave similar profiles suggesting that also the duration of immunity is not influenced.

In conclusion, the antibody responses after associated mixed use of Porcilis PRRS and Porcilis Ery+Parvo+Lepto were at least as high as after vaccination with either vaccine alone and therefore, it can be concluded that the take of the vaccines and the level of immunity are not negatively influenced by the associated mixed use. Likewise, the decline in antibody titre over time showed similar profiles indicating that the duration of immunity for all vaccine components also is not negatively influenced by the association.

Experiment 4: PRRS Efficacy at a Minimum Dose in a Combination Vaccine with Ery+Parvo+Lepto The objective of this experiment was to evaluate the efficacy of a live attenuated PRRSV Type 2 vaccine (Prime Pac® PRRS) reconstituted at the minimal dose of 4.0 log 10 TCID50/animal in an EPL vaccine.

Sixty-six 5-week-old piglets seronegative for PRRSV were included in this study. The piglets were vaccinated with a minimal dose of Prime Pac® PRRS reconstituted in either an EPL formulation (group 1; one hour of waiting time at 25° C. between reconstitution and vaccination) or in Diluvac Forte (group 2), intramuscularly in the right side of the neck. Piglets in group 3 were vaccinated intramuscularly in the right side of the neck with 2 ml of the same EPL formulation and served as PRRSV-challenge controls. At 4 weeks post vaccination the piglets were challenged with a dose of 5.0 log 10 TCID50 of a virulent PRRSV Type 2 strain, Nebraska-1, by the intranasal (IN) route, 1 ml per nostril. Blood samples from the piglets were taken at day of vaccination, day of challenge, 5, 7, 10, 14 and 28 days post challenge. Rectal temperatures were measured on 1 day before challenge, just before challenge, 4 hours post challenge, and thereafter daily from 1 until 10 days post challenge. Bodyweight were measured on the day before challenge, 9 and 25 days post challenge. On 10 days post challenge 11 pigs per group were euthanized and observed for lung lesions. On 28 days post challenge the remaining piglets were euthanized.

Body Temperature and Body Weight

With regard to body temperature, in each of the vaccine groups the temperature was lower than in the control group 3. It was also found that there is no difference between the mixed use group 1 and the Prime Pac® PRRS only group (group 2). With regard to the body weight, the vaccinated animals grew faster than the unvaccinated animals in group 3. It was also found that the animals in the mixed use group 1 grew at a similar rate as the animals in the Prime Pac® PRRS only group (group 2).

Lung Lesions Scores

Half of the animals, in total 11 animals per group, were euthanized at 10 days post challenge to observe their lungs for PRRS related pneumonia. Table 3 shows per group the mean estimated percentage of the lung affected with visible pneumonia. From the table it can be concluded that in general the PRRSV challenge strain caused on average hardly any lung lesions. Nevertheless, at 10 days post vaccination, the vaccinated animals showed fewer lung lesions than the controls. Overall, not much difference was seen between the mixed use group and the Prime Pac® PRRS only group.

TABLE 3

Mean lung lesion scores per group, 10 dpc

| Group | 10 dpc |
| --- | --- |
| PrimePac + EPL | 0 |
| PrimePac | 0.2 |
| Control | 0.85 |

Serological Response

On the day of vaccination all animals were seronegative for PRRSV, demonstrating that PRRSV negative animals were used for this study. Animals in the unvaccinated control group remained seronegative until the day of challenge (i.e. 4 weeks post vaccination). In contrast, on the day of challenge an antibody response was measured for the vaccinated groups, indicating that the animals in both the mixed use group 1 and the Prime Pac® PRRS only group (group 2) were successfully primed by PRRS vaccination. At later time points post challenge, i.e. 10 and 28 dpc, an increase in the height of the antibody level was observed, most likely caused by the challenge infection.

PRRS Viremia

The mean virus titer per group is represented in table 4. The table clearly shows that the vaccinated animals (group 1 and 2) have on average a reduced virus load in their serum as compared to the control animals (group 3). There is little difference in height of the viremia between each of the vaccinated groups.

TABLE 4

| | PRRS titer dpc, log10 TCID50/ml | | | | | |
|---|---|---|---|---|---|---|
| Group | 0 | 5 | 7 | 10 | 14 | 28 |
| 1 | 0 | 0.6 | 0.5 | 0.7 | 0.6 | 0 |
| 2 | 0 | 0.1 | 0.2 | 0.2 | 0.3 | 0 |
| 3 | 0 | 2.0 | 1.8 | 2.2 | 2.1 | 0 |

In conclusion, it has been established that even in the lowest dose (i.e. the lower limit according to the label) the commercial vaccine Prime Pac® PRRS reconstituted in an EPL formulation adequately seroconverted animals, and protection against pathogenic PRRSV is obtained.

The invention claimed is:

1. A method for prophylactically treating a swine that is seronegative for PRRS virus against an infection with *Erysipelothrix rhusiopathiae*, porcine parvo virus, *Leptospira interrogans*, and PRRS virus comprising administering a vaccine comprising a pharmaceutically acceptable carrier and a non-replicating immunogen of an *Erysipelothrix rhusiopathiae*, a non-replicating immunogen of a porcine parvo virus, a non-replicating immunogen of a *Leptospira interrogans*, and a live attenuated PRRS virus;
wherein the vaccine is administered in a single dose with regard to the treatment against an infection with PRRS virus to said swine that is seronegative for PRRS virus.

2. The method of claim 1, wherein the non-replicating immunogen of the *Erysipelothrix rhusiopathiae*, the non-replicating immunogen of the porcine parvo virus, and the non-replicating immunogen of the *Leptospira interrogans* are inactivated pathogens of the *Erysipelothrix rhusiopathiae*, the porcine parvo virus, and the *Leptospira interrogans*, respectively.

3. The method of claim 1, wherein the *Leptospira interrogans* pathogen comprises bacteria of the serogroup Pomona.

4. The method of claim 3, further comprising a bacterium selected from the serogroup consisting of a Tarassovi, an *Australis*, a Grippotyphosa, an Icterohaemorrhagiae, and a Canicola.

5. The method of claim 4, wherein the bacterium of the *Australis* is from a serovar Bratislava.

6. The method of claim 1, wherein the vaccine is administered parenterally.

7. The method of claim 1, wherein the vaccine is administered intramuscularly.

8. A kit for a swine that is seronegative for PRRS virus comprising a combination vaccine and a set of instructions; wherein the combination vaccine comprises a first vaccine comprising a pharmaceutically acceptable carrier and a non-replicating immunogen of an *Erysipelothrix rhusiopathiae*, a non-replicating immunogen of a porcine parvo virus, and a non-replicating immunogen of a *Leptospira interrogans* and a second vaccine comprising a freeze-dried live attenuated PRRS virus; and wherein the set of instructions state that:
  (i) the second vaccine is to be mixed with the first vaccine to form the combination vaccine; and
  (ii) the combination vaccine is to be administered to said swine that is seronegative for PRRS virus in a single dose with regard to the treatment against an infection with PRRS virus.

9. The kit of claim 8, wherein the non-replicating immunogen of the *Erysipelothrix rhusiopathiae*, the non-replicating immunogen of the porcine parvo virus, and the non-replicating immunogen of the *Leptospira interrogans* are inactivated pathogens of the *Erysipelothrix rhusiopathiae*, the porcine parvo virus, and the *Leptospira interrogans*, respectively.

* * * * *